US010448918B2

United States Patent
Broggio et al.

(10) Patent No.: US 10,448,918 B2
(45) Date of Patent: Oct. 22, 2019

(54) THYROID PHANTOM, CORRESPONDING PRODUCTION METHOD, OVERALL PHANTOM COMPRISING SUCH A THYROID PHANTOM AND CORRESPONDING PHANTOM FAMILIES

(71) Applicant: INSTITUT DE RADIOPROTECTION ET DE SURETE NUCLEAIRE, Fontenay Aux Roses (FR)

(72) Inventors: David Broggio, Clamart (FR); Tiffany Beaumont, Villejuif (FR)

(73) Assignee: INSTITUT DE RADIOPROTECTION ET DE SURETE NUCLEAIRE, Fontenay Aux Roses (FR)

( * ) Notice: Subject to any disclaimer, the term of this patent is extended or adjusted under 35 U.S.C. 154(b) by 0 days.

(21) Appl. No.: 16/072,591

(22) PCT Filed: Jan. 26, 2017

(86) PCT No.: PCT/EP2017/051605
§ 371 (c)(1),
(2) Date: Jul. 25, 2018

(87) PCT Pub. No.: WO2017/133957
PCT Pub. Date: Aug. 10, 2017

(65) Prior Publication Data
US 2019/0029633 A1    Jan. 31, 2019

(30) Foreign Application Priority Data

Feb. 3, 2016  (FR) .................................... 16 50855

(51) Int. Cl.
*A61B 6/00*      (2006.01)
*G09B 23/30*    (2006.01)

(52) U.S. Cl.
CPC .............. *A61B 6/583* (2013.01); *G09B 23/30* (2013.01); *A61B 6/5294* (2013.01)

(58) Field of Classification Search
CPC ........ A61B 6/583; A61B 6/5294; G09B 23/30
(Continued)

(56) References Cited

U.S. PATENT DOCUMENTS 5,222,021 A  *  6/1993  Feldman ................ A61B 6/583
                                                           378/18
5,227,627 A      7/1993  Gamarnik et al.
(Continued)

FOREIGN PATENT DOCUMENTS

DE    196 28 997 C1    10/1997
EP    2 977 008 A1      1/2016
JP    2014-215222 A    11/2014

OTHER PUBLICATIONS

Anonymous: "Thyroid Phantom", Aug. 7, 2014, XP055304837, Retrieved from the Internet: URL:http://www.jzimaging.com/Biodex_thyroid_phantom.htm [retrieved on Sep. 22, 2016].
(Continued)

*Primary Examiner* — Marcus H Taningco
*Assistant Examiner* — Blake C Riddick
(74) *Attorney, Agent, or Firm* — Sughrue Mion, PLLC (57) ABSTRACT

The invention concerns a thyroid phantom (1), the phantom comprising a body (2) comprising at least two parts (3, 4) defining between them an imprint (7) of a thyroid and means for attaching the two parts together in order to close the imprint in a sealed manner, the phantom further comprising means for filling the imprint with a solution, said filling means comprising at least one channel (19, 20) extending from the outside of the body into the imprint and means for temporarily symmetrically plugging said channel. The invention also concerns a method for producing such a (Continued)

thyroid phantom, a family comprising a plurality of such thyroid phantoms corresponding to different categories of human beings, an overall phantom comprising one such thyroid phantom as well as a family comprising a plurality of overall phantoms.

20 Claims, 3 Drawing Sheets (58) Field of Classification Search
USPC .......................... 250/252.1, 363.04, 363.02
See application file for complete search history.

(56) References Cited

U.S. PATENT DOCUMENTS

| | | | | |
|---|---|---|---|---|
| 6,831,269 | B2* | 12/2004 | Zyromski | A61K 51/1268 250/252.1 |
| 2012/0330083 | A1* | 12/2012 | Aitkenhead | A61N 5/1071 600/1 |
| 2016/0073990 | A1 | 3/2016 | Nakajima et al. | |
| 2016/0278735 | A1* | 9/2016 | Franke | A61B 5/055 |

OTHER PUBLICATIONS

Anonymous: "Med Equipment Platform Thyroid phantom", Jan. 1, 2014, XP055304851, Retrieved from the Internet: URL:http://images.google.de/imgres?imgurl=http://www.medwow.com/med/nuclear-medicine-phantom/nuclear-associates/74-340-thyroid/x74-340-thyroid.mth21500_200_200.jpg.pagespeed.ic.sRZh5qSuUm.jpg&imgrefurl=http://www.medwow.com/med/nuclear-medicine-phantom/nuclear-associates/74-340-thyroid/21500.model-spec& [retrieved on Sep. 22, 2016].

International Search Report of PCT/EP2017/051605 dated May 17, 2017 [PCT/ISA/210].

* cited by examiner

THYROID PHANTOM, CORRESPONDING PRODUCTION METHOD, OVERALL PHANTOM COMPRISING SUCH A THYROID PHANTOM AND CORRESPONDING PHANTOM FAMILIES

CROSS REFERENCE TO RELATED APPLICATIONS

This application is a National Stage of International Application No. PCT/EP2017/051605, filed Jan. 26, 2017, claiming priority based on French Patent Application No. 16 50855, filed Feb. 3, 2016.

The invention relates to a thyroid phantom. The invention also relates to a method for producing such a thyroid phantom. The invention also relates to an overall phantom comprising such a thyroid phantom. The invention also relates to a family comprising several such thyroid phantoms. The invention also relates to a family comprising several such overall phantoms.

BACKGROUND OF THE INVENTION

Thyroid anthroporadiometry consists in measuring X-ray or γ radiation emitted by the thyroid as radionuclides contained in the thyroid decay. The experimental measurement thus acquired is compared against a reference measurement, also referred to as a benchmark measurement, and this makes it possible to deduce the various radionuclides present in the thyroid, and the activity thereof.

The reference measurement is usually obtained by performing an anthroporadiometric study on one or more digital or physical phantoms. These phantoms are digital or physical objects that more or less schematically represent the thyroid and are generally filled with a solution which acts as a radiation emission source, which source proves to be of known nature and activity.

This type of thyroid phantom is incidentally used in medical imaging and dosimetry fields other than anthroporadiometry.

OBJECT OF THE INVENTION

One object of the invention is to offer a physical thyroid phantom that is relatively simple to produce and to use and which furthermore proves to be relatively realistic from an anatomical standpoint. One object of the invention is also to offer a method for producing such a thyroid phantom. One object of the invention is also to offer an overall phantom comprising such a thyroid phantom. One object of the invention is also to offer a family comprising several such thyroid phantoms. Another object of the invention is to offer a family comprising several such overall phantoms.

BRIEF DESCRIPTION OF THE INVENTION

In order to meet these objectives, the invention proposes a thyroid phantom, the phantom comprising a body comprising at least two parts between them defining a thyroid cavity and means for fixing the two parts together to close the cavity in a sealed manner, the phantom further comprising means for filling the cavity with a solution, said filling means comprising at least one canal extending from outside the body into the cavity and means for temporarily hermetically plugging said canal.

In that way, the thyroid phantom can be produced relatively easily by independently creating these two body parts and fixing these two parts together. In particular, the two parts of the body of the thyroid phantom can be produced separately by three-dimensional printing, and this allows for relatively easy and repeatable production of the phantom.

In addition, once assembled, the phantom can just as easily be filled with solution as left empty. It thus proves possible to supply a customer directly with the phantom or with the phantom with a particular solution inserted into the phantom. It is also conceivable to fill the phantom with a particular solution, for example a radioactive solution, to close the phantom hermetically at the filling canal before delivering the entire entity to a customer who does not have the ability or required clearances to source this solution directly.

This makes the phantom easier for the customer to use.

In addition, the phantom proves to be relatively realistic from an anatomical standpoint, because of the thyroid cavity.

The invention also relates to a method for producing such a phantom, comprising the following successive steps: three-dimensional digital modeling of the body of the thyroid phantom, separate manufacture of each part of the body by three-dimensional printing using a 3D printer, cleaning, off each part of the body thus created, a lost material used by the 3D printer to form the cavity, assembling the two parts of the body with one another.

The invention also relates to a thyroid phantom family comprising at least two thyroid phantoms as described hereinabove, each thyroid phantom being suited to simulating at least the thyroid of a distinct particular category of human beings.

The invention also relates to an overall phantom comprising a thyroid phantom as described hereinabove, the overall phantom comprising a neck phantom receiving the thyroid phantom, a cervical vertebrae phantom received in the neck phantom and a spinal cord phantom received in the cervical vertebrae phantom.

The invention also relates to an overall phantom family comprising at least two overall phantoms as described hereinabove, each overall phantom being suited to simulating at least the thyroid of a distinct particular category of human beings.

BRIEF DESCRIPTION OF THE DRAWINGS

The invention will be better understood in the light of the following description of one nonlimiting particular embodiment of the invention.

Reference will be made to the attached figures in which.

DETAILED DESCRIPTION OF THE INVENTION

Figure 1:
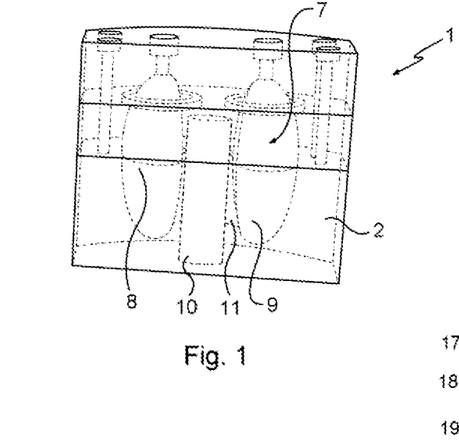
FIG. 1 is a perspective view of the thyroid phantom according to one particular embodiment of the invention, the internal elements of the phantom being visible in dotted line.
Figure 2:
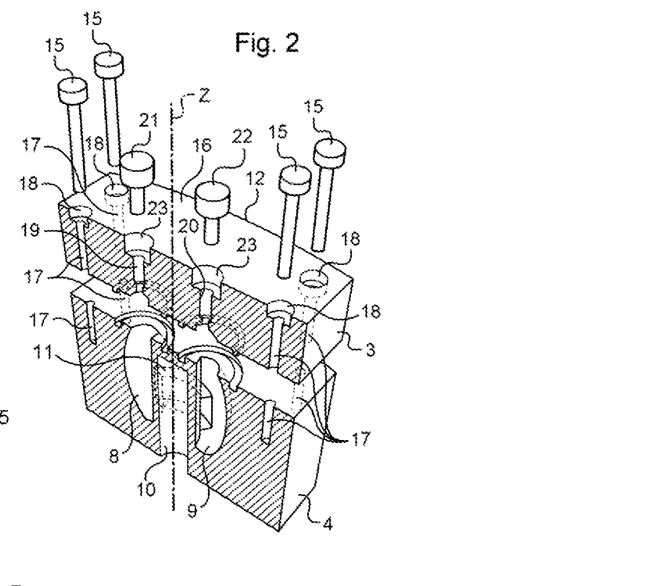
FIG. 2 is a cross-sectioned perspective view of the phantom illustrated in FIG. 1, the view being an exploded view of said phantom.
Figure 3:
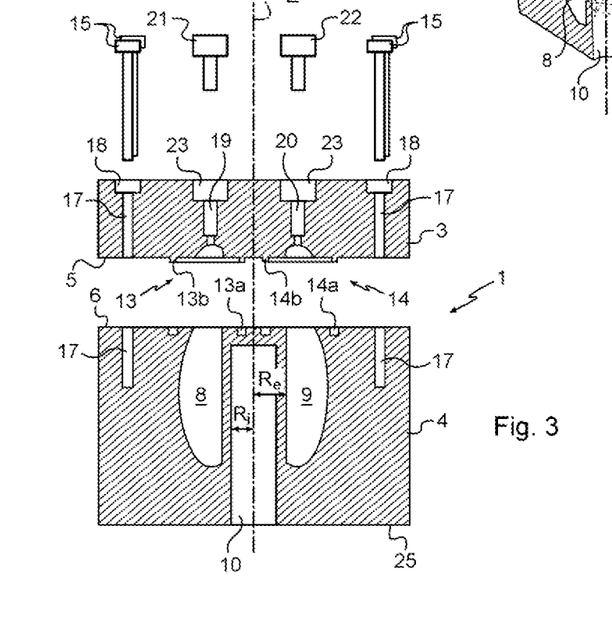
FIG. 3 is a face-on view of the cross section depicted in FIG. 2.

With reference to FIGS. 1 to 3, the thyroid phantom according to the invention, denoted generally by 1, is intended here to be used for benchmarking anthroporadiometric measurements. Of course this application is nonlimiting and said phantom could be used in the context of other applications such as for benchmarking other imaging and dosimetry forms, notably, although not exclusively, in the field of medicine, just as in the field of nuclear medicine or radio protection.

The thyroid phantom 1 comprises a body 2 which in this instance is made up of a first part 3 and of a second part 4. The lower face 5 of the first part 3 rests on the upper face 6 of the second part 4, said faces being of the same dimensions. The body 2 is thus configured in such a way that said faces (and therefore the boundary between the two parts) extend in a plane normal to an axis Z. The axis Z here is substantially vertical, which means to say that said faces extend substantially horizontally. The axis Z thus symbolizes the head-feet direction of a human body.

The body 2 is preferably made from a material capable of being used by a three-dimensional printer.

The body 2 in this instance is made of a polymer material.

For preference, the body 2 is made from a material which is also transparent. This allows the various elements internal to the body 2 to be monitored, as will be seen later.

For preference, the body 2 is made from a material that has X-ray or gamma ($\gamma$)-ray transmission properties similar to those of human tissues.

The body 2 is, for example, based on polymethylmethacrylate or on polycarbonate.

The two parts 3, 4 are configured in such a way as to define between them a closed cavity 7 representative of a thyroid of a human body. It will be recalled that the thyroid of a human body has the overall shape of a bow-tie and is thus made up of two symmetrical lobes situated one each side of the trachea, the two lobes being connected by a band of tissue referred to as the isthmus. The cavity 7 in this instance is configured in such a way as to comprise two lobes 8, 9 separated from one another by a cylinder 10 of axis Z of the body 2 simulating a human trachea (the cylinder therefore not forming part of the cavity 7).

For preference, said cylinder 10 is hollowed out on the inside so as to form a tube extending along the axis Z and opening only at the lower face 25 of the second part 4 (the other end of the cylinder 10 therefore not opening onto the upper face 6 of the second part 4). Formed in this way, the cylinder 10 therefore does not open into the cavity 7. The cylinder 10 has an external radius $R_e$ and an internal radius $R_i$. Each lobe 8, 9 thus has the overall shape of an ellipsoid with an axis of revolution parallel to the axis Z (the two lobes 8, 9 are thus vertical) delimited at its surface that faces the other lobe by the cylindrical surface of axis Z. The two lobes 8, 9 are therefore symmetric about the axis Z. Each lobe 8, 9 is, for example, defined from the following general equations:

$$\left(\frac{x-x_0}{a}\right)^2 + \left(\frac{y-y_0}{b}\right)^2 + \left(\frac{z-z_0}{c}\right)^2 \leq 1$$

$$x^2 + (y-y_0)^2 \geq R_e^2$$

$R_e$ being the external radius of the trachea and $x_0$, $y_0$, $z_0$, a, b and c parameters defining the relevant lobe.

The cavity 7 is also configured in such a way as to connect the lower ends of the two lobes 8, 9 by an isthmus 11. The isthmus 11 in this instance is configured as a portion of an annulus one end of which opens into one of the lobes 8 and the other end of which opens into the other of the lobes 9. However, the isthmus 11 does not open into the cylinder 10.

The annulus portion is thus in this instance arranged in such a way as to have a center of revolution arranged on the axis Z and to have an internal radius equal to $R_e$. The internal face of the annulus portion therefore ensures continuity of the cavity 7 between the curved face of the first lobe 8 and the curved face of the second lobe 9.

This annulus portion is, for example, defined from the following equations:

$$R_e^2 \leq x^2 + (y-y_0)^2 \leq R_{isth}^2$$

$$z - h_{isth} \leq z \leq z_0$$

$$y \leq y_0$$

$R_{isth}$ being the external radius of the annulus portion ($R_e$ being the internal radius of the annulus portion equal to the external radius of the cylinder 10) and $h_{isth}$ the height of the annulus portion.

The cavity 7 thus described comprises the two lobes 8, 9 and the isthmus 11 and is closed.

The abovementioned equations describing the cavity come from the Ulanovsky and Eckerman model (described in particular in the article entitled "Absorbed fractions for electron and photon emissions in the developing thyroid: fetus to five years old" published in Radiation Protection Dosimetry volume 79, Nos 1-4, pp. 419-424 in 1998).

For preference, these Ulanovsky and Eckerman models are adapted to adhere to the new recommendations from the International Commission on Radiological Protection (better known by the acronyms ICRP, or CIPR in French), on the understanding that the Ulanovsky and Eckerman models are based on earlier ICRP recommendations. This adaptation can be achieved for example by applying a scaling factor to the Ulanovsky and Eckerman models in order to follow the new recommendations.

For preference also, these Ulanovsky and Eckerman models are adapted to take account of the nature of any solution that may potentially be arranged in the cavity 7, notably an acid and/or radioactive solution. Steps will thus be taken to ensure that the distance separating the cavity 7 from the outside is great enough that the corresponding walls can withstand attack by the solution (particularly at the wall that forms the cylinder 10). The two parts 3, 4 of the body 2 are in this instance arranged in such a way that their boundary extends through the upper ends of the two lobes 8, 9. The lobes 8, 9 are therefore predominantly created in the second part 4 and only to a minor extent created in the first part 3, and the isthmus 11 is wholly created in the second part 4 of the body 2.

According to one preferred embodiment, the body 2 is configured in such a way as to exhibit the overall shape of a rectangular parallelepiped, of which one main lateral face 12 (as opposed to the upper and lower faces of the body 2 which are normal to the axis Z) being rounded in order to simulate the curvature of a neck of a human body.

This allows the thyroid phantom 1 to be more representative of a human body, making it possible to obtain better reference measurements using said phantom.

For preference, the body 2 in this instance is also configured in such a way as to take into consideration the thyroid-neck distance of a human body, namely the distance separating the thyroid isthmus from the surface of the neck (in the case of the body 2, said distance is simulated by the distance separating the cavity 7 from the main lateral face 12).

For preference also, the body 2 is also configured in such a way as to take into consideration the attenuation of the rays emitted by a human thyroid in the adipose tissues surrounding said thyroid.

Thus, the position of the cavity 7 relative to the rounded lateral face 12 of the body 2 is configured so that it at once takes into account a thyroid-neck distance of a human body, the material of which the thyroid phantom 1 is formed, and the physical characteristics of the adipose tissues of a human body, as will be seen later on.

This allows the thyroid phantom 1 to be more representative of a human body, making it possible to obtain better reference measurements using said phantom.

The thyroid phantom 1 comprises means for fixing the two parts 3, 4 of the body together to close the cavity 7 in a sealed manner.

Thus, the thyroid phantom 1 is configured in such a way as to be able to be filled with a solution.

For preference, the fixing means comprise a first fitting-together system 13 and a second fitting-together system 14, each comprising a female portion 13a, 14a and a male portion 13b, 14b, one of the portions being borne by the first part 3 at the boundary between the two parts 3, 4 and the other of the portions being borne by the second part 4 facing the other portion at the boundary between the two parts 3, 4 in order to allow the two portions to be fitted together.

That allows the two parts of the body 2 to be interlocked together correctly. This then improves the sealing of the thyroid phantom 1, particularly at a critical zone that is the boundary of the cavity 7.

In particular, the female portions 13a, 14a are orifices in the form of a loop (according to the axis Z) created in one of the parts, and the male portions 13b, 14b are corresponding raised loops extending from the other of the parts. The portions are arranged in such a way that the first fitting-together system 13 passes around the upper end of the first lobe 8 and that the second fitting-together system 14 passes around the upper end of the second lobe 9. Thus, for each fitting-together system 13, 14, the male portion and the female portion each pass around the corresponding lobe on respectively one or other of the upper face 6 of the second part 4 and the lower face 5 of the first part 3.

The loops are, for example, in the form of a circular annulus or in the form of an elliptical ring.

In particular, the fixing means further comprise screws 15 used to secure the two parts 3, 4 together in a sealed manner.

The fixing means comprise for example four screws 15 which are arranged at the four corners of the upper face 16 of the first part 3 and the shanks of which extend, from the first part 3 into the second part 4, in a respective direction parallel to the direction Z. The screws 15 are arranged in such a way that the upper surfaces of the screw heads lie flush with the upper face 16 of the first part 3. The body 2 therefore comprises four orifices 17 to receive the shanks of the screws 15 (and which are therefore made in the first part 3 and in the second part 4) and four housings 18 at the upper ends of said orifices 17 (and therefore created in the first part 3) to receive the corresponding screw heads.

For preference, the fixing means further comprise adhesive (not visible here) arranged between the head of each screw 15 and the bottom of the housing 18 receiving said screw 15 head.

This makes it possible to improve the fixing of the two parts 3, 4 of the body 2.

For preference, said adhesive is made from a material resistant to acids.

The adhesive in this instance is based on polymethylmethacrylate, on polycarbonate, or on a polyepoxy (which is a mixture of an epoxy resin with a hardener). The adhesive is, for example, Araldite adhesive (registered tradename).

For preference, the fixing means further comprise adhesive (not visible here) arranged inside the fitting-together systems 13, 14.

This makes it possible to improve the fixing of the two parts 3, 4 of the body 2.

For preference, said adhesive is made from a material resistant to acids.

The adhesive in this instance is based on polymethylmethacrylate, on polycarbonate, or on a polyepoxy (which is a mixture of an epoxy resin with a hardener). The adhesive is, for example, Araldite adhesive (registered tradename).

The thyroid phantom 1 further comprises means for filling the cavity 7 (the two lobes 8, 9 and the isthmus 11) with a solution from outside the thyroid phantom 1.

Said filling means comprise a first canal 19 extending from the upper face 16 of the first part 3 as far as into the upper end of the first lobe 8, and a second canal 20 extending from the upper face 16 of the first part 3 as far as into the upper end of the second lobe 9.

The filling means also comprise means for temporarily hermetically plugging the first canal 19 and the second canal 20.

For that purpose, the plugging means comprise a first screw 21 for plugging the first canal 19 and a second screw 22 for plugging the second canal 20. The filling means are thus configured in such a way that the upper surfaces of the screw heads lie flush with the upper face 16 of the first part 3 of the body 2. The two canals 19, 20 therefore each comprise a housing 23 at the upper end of the relevant canal, to receive the corresponding screw head.

The screws 21, 22 of the filling means are preferably made from a material that is resistant to acids. For preference, the screws 21, 22 of the filling means are also made from a material that diffuses or absorbs X-rays or gamma γ-rays little if at all.

In that way, the thyroid phantom 1 is configured in such a way as to be able to be filled with a radioactive solution.

That allows the thyroid phantom 1 to provide benchmarking measurements that are even more precise during an anthroporadiometric study.

For preference, the screws 15 of the plugging means are also made from a material resistant to acids. For preference also, the screws 15 of the plugging means diffuse or absorb X-rays or gamma-rays little if at all.

All the screws of the plugging means and of the filling means 15, 21, 22 are, for example, made of nylon.

The plugging means also comprise first seal (not visible here) arranged in the first canal 19 between the screw head 21 and the bottom of the housing 23 and compressed by said screw head 21 against the bottom of the housing 23, and a second seal (not visible here) arranged in the second canal 20 between the screw head 22 and the bottom of the housing 23 and compressed by said screw head 22.

For preference, said seals are made from a material of a hardness lower than that forming the body 2. For preference also, said seals are made from a material resistant to acid.

This means that a durable seal can be achieved.

The seals are, for example, based on rubber. For example, the seals are based on synthetic rubber from the fluorinated elastomer family. The seals in this instance are made of Viton (registered tradename)

According to one preferred embodiment, the thyroid phantom 1 contains a solution (not visible here) filling the cavity 7 of the thyroid phantom 1.

The solution is preferably a radioactive solution.

For preference, the solution comprises at least one radionuclide simulating at least one of the emission lines of iodine 131 ($^{131}$I) and having a longer lifetime than iodine 131.

Specifically, iodine 131 is a radionuclide released in high concentrations into the atmosphere in the event of a nuclear incident and that becomes readily fixed in the human thyroid. Furthermore, the emission spectrum for iodine 131 comprises a relatively high energy line at 365 kiloelectron-volts (82% emission) which is attenuated little if at all by the tissues of a human body, notably the adipose tissues surrounding the thyroid. As a result, the detection of iodine 131 is a relatively easy matter using anthroporadiometry. It is therefore advantageous for the thyroid phantom 1 to be able to be adapted to providing a reference measurement connected with this radionuclide. However, iodine 131 has a lifetime of approximately 8.0228 days, which is not long enough for the iodine 131 to be able to be used directly in the solution filling the thyroid phantom.

In particular, the solution contains by way of radionuclide barium 133 ($^{133}$Ba).

Such a radionuclide has a lifetime of approximately 10½ years, which means that it can be used is the thyroid phantom. Furthermore, barium 133 has an emission spectrum exhibiting a likewise high energy line of 356 kiloelectron-volts (62% emission) which means that it correctly simulates the way in which iodine 131 behaves.

The concentration of barium 133 in the solution is for example comprised between 100 and 130 becquerel per gram to simulate a child thyroid and between 35 and 40 becquerel per gram to simulate an adult thyroid.

For preference, the solution also contains at least one acid component so as to place the barium 133 in as acidic environment.

This makes it possible to ensure that the solution remains stable and homogeneous in the presence of the barium 133 radionuclide.

The acid component is, for example, hydrochloric acid. The concentration of hydrochloric acid in the solution is comprised for example between 2 and 16% and preferably between 2 and 5%.

Figure 4:
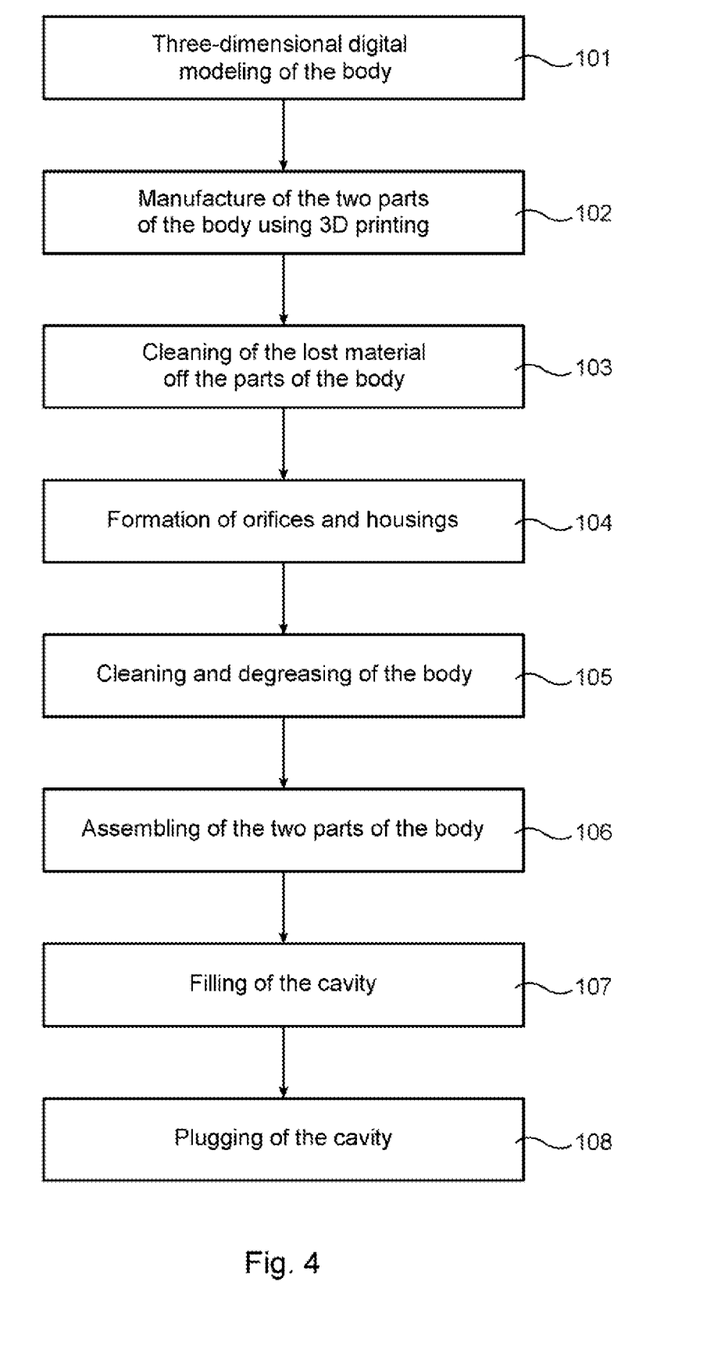
FIG. 4 is a diagram indicating the various steps in the method for producing the thyroid phantom as illustrated in FIG. 1.

The method for producing the thyroid phantom 1 will now be described with reference to FIG. 4.

The first step 101 is to create a three-dimensional digital model of the body 2 of the thyroid phantom 1, with the help of the aforementioned equations, is order to model the cavity 7, namely:

$$\left(\frac{x-x_0}{a}\right)^2 + \left(\frac{y-y_0}{b}\right)^2 + \left(\frac{z-z_0}{c}\right)^2 \leq 1$$

$$x^2 + (y-y_0)^2 \geq R_e^2$$

$$R_e^2 \leq x^2 + (y-y_0)^2 \leq R_{isth}^2$$

$$z - h_{isth} \leq z \leq z_0$$

$$y \leq y_0$$

The position of the cavity 7 in the body 2 is also modeled, therefore taking into account a thyroid-neck distance of a human body, the material of which the thyroid phantom 1 is made and the physical characteristics of the adipose tissue of a human body, using the following relationship:

$$x = x_{tissue} * (\mu_{tissue}/\mu)$$

where x is the thyroid-neck distance of the thyroid phantom 1, $x_{tissue}$ is the thyroid-neck distance of a human body, $\mu$ is the linear attenuation coefficient for the material from which the body of the thyroid phantom 1 is to be formed, and $\mu_{tissue}$ is the linear attenuation coefficient for the adipose tissue of a human body surrounding a human thyroid.

The dimensions of the body 2, of the cavity 7 and the relative position of the cavity 7 in the body 2 are also adapted according to the type of category of individual to be targeted in the measurements made by the thyroid phantom 1 thus produced. For example, if the desire is to create a thyroid phantom 1 for an adult man, the various dimensions and the relative position of the cavity 7 in the body 2 will be different than if the desire is to create a thyroid phantom 1 of a child.

The ICRP recommendations notably allow the aforementioned equations to be adapted to suit the type of patient targeted in terms of the dimensions of the cylinder 10 of the body 2, of the cavity 7 and in terms of the relative position of the cavity 7 in the body 2.

In particular, said recommendations and the type of energy line that is to be studied using the thyroid phantom make it possible to estimate $x_{tissue}$ and $\mu_{tissue}$. For a high energy line of 356 kiloelectron-volts (corresponding to that of the barium 133 used in this instance), a linear attenuation coefficient for the adipose tissue $\mu_{tissue}$ of 0.1056 centimeter$^{-1}$ is, for example, adopted. Also, for example, a thyroid-neck distance $x_{tissue}$ of 0.5 centimeter is adopted for an adult.

The second step 102 is to produce each part 3, 4 of the body 2 separately by three-dimensional printing using a 3D printer. As is known per se, the 3D printer is going to use a lost material, such as a gel or a resin, for creating the cavity 7 inside the parts 3, 4 of the body 2.

The third step 103 consists in cleaning, off each part 3, 4 of the body 2 thus created, the lost material that was covering or filling said parts. This step 103 is performed for example using a high pressure waterjet. Note that the fact that the body 2 is constructed in two parts 3, 4 means that the lost material can be cleaned off said body 2 quickly and easily.

The fourth step 104 consists in forming the orifices (for example by boring) and the housings intended to receive the four screws 15 of the fixing means and the two screws 21, 22 of the filling means.

A fifth step 105 consists in cleaning and degreasing the body.

The sixth step 106 consists in assembling the two parts 3, 4 of the body 2 together. The adhesive is applied to each housing 18 and to the fitting-together systems 13 and 14, the two parts 3, 4 of the body 2 are then interlocked in one another at the fitting-together systems 13, 14 then the screws 15 of the fixing means are arranged inside the orifices 17. It will be noted that the interlocking of the two bodies 3, 4 at the fitting-together systems 13, 14 makes the subsequent insertion of the screws 15 easier.

The seventh step 107 in this instance consists in filling the cavity 7 with the solution. For example, the solution is contained in a syringe which is inserted into the body 2 at each filling canal 19, 20 in turn until it reaches the cavity 7. The content of the syringe is then emptied into the cavity 7.

The eighth step 108 finally consists in plugging the filling canals 19, 20 by fitting first of all the seals and then screwing the screws 21, 22 into the two canals 19, 20 to seal the cavity 7 hermetically.

Figure 5:
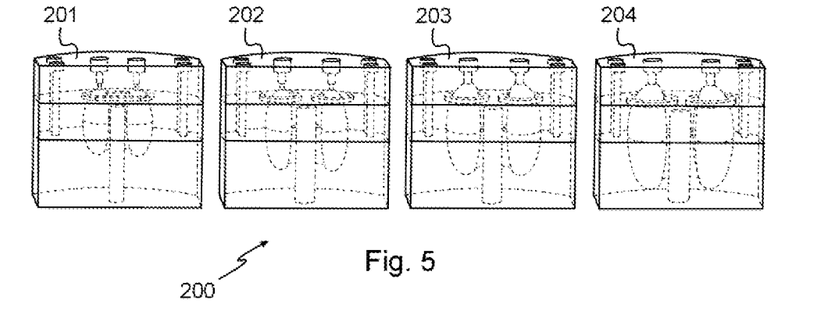
FIG. 5 is a perspective view of a series of thyroid phantoms, a family comprising the thyroid phantom as illustrated in FIG. 1.

For preference, as visible in FIG. 5, the method according to the invention is performed in such a way as to produce a family 200 of thyroid phantoms as described earlier, each phantom being intended to act as a benchmark for reference measurements for a particular age group of patients. In this instance, a family 200 of four phantoms is produced: a first phantom 201 associated with a five-year-old patient, a second phantom 202 associated with a 10-year-old patient, a third phantom 203 associated with a 15-year-old patient, and a fourth phantom 204 associated with an adult patient.

The dimensions of each phantom (notably the dimensions of the cavity, of the body, and of the distance between the isthmus and the rounded face 12 of the body symbolizing the neck-thyroid distance fixed by the transmission properties of the material of the phantom 1) are thus adapted so as to simulate the thyroid of a patient of the age to which that phantom relates.

It is thus possible to take multiple reference measurements. Advantageously, each thyroid phantom thus proves itself to be more representative of a human body of a particular category thereby making it possible to obtain better reference measurements using said phantom.

Figure 6:
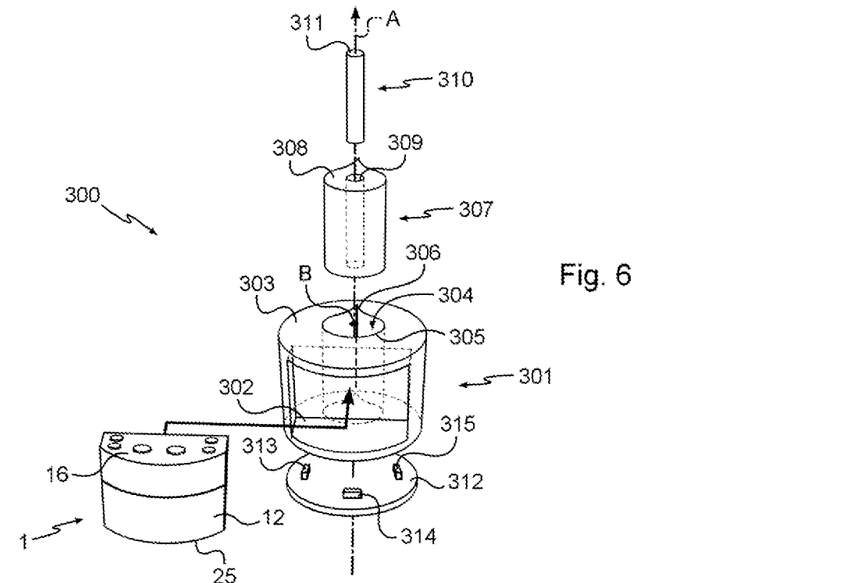
FIG. 6 is an exploded perspective view of an overall phantom comprising the thyroid phantom illustrated in FIG. 1.

With reference to FIG. 6 and for preference, the thyroid phantom 1 is inserted into an overall phantom 300.

The overall phantom 300 comprises a neck phantom 301 intended to simulate the neck of a human body comprising the thyroid, which in this instance is configured as a cylinder with an axis of revolution. A parallel to the axis Z.

The cylinder is for example defined by the following equations:

$$x^2+y^2 \leq R_H^2$$

$$C_T \leq z \leq C_T + C_{HO}$$

where $R_H$ is the radius of the cylinder and $C_{HO}$ is the height of the cylinder, $C_T$ corresponding to a feet-trunk distance of a patient associated with said neck phantom.

The aforementioned neck equations and the $C_T$ values are described in greater detail for example in the article "Description of the mathematical phantoms" available on the web page https://crpk.ornl.gov/resources/Mird.pdf and published by Oak Ridge National Laboratory in 2005.

The neck phantom 301 comprises a first housing 302 in which the thyroid phantom 1 is received. This first housing 302 is formed in the cylinder in such a way that the rounded lateral face 12 of the thyroid phantom 1 itself forms a portion of the lateral face of the cylinder, the lateral face of the thyroid phantom 1 opposite to this rounded face 12 then resting against the inside of the cylinder. The first housing 302 is also configured in such a way that the upper face 16 of the first part 3 of the thyroid phantom 1 rests against the inside of the cylinder and in such a way that the lower face 25 of the second part 4 of the thyroid phantom 1 rests against the inside of the cylinder.

In particular, the overall phantom 300 comprises a base 312 on which the neck phantom 301 rests.

The base 112 is configured in this instance as a cylinder of axis of revolution. A with the same radius $R_H$ as the radius of the cylinder of the neck phantom 301. The base 112 thus forms an extension of the neck phantom 301.

For preference, the neck phantom 301 comprises means for fixing to the base 312.

Typically, the fixing means comprise a first fitting-together system 313, a second fitting-together system 314, and a third fitting-together system 315. Each fitting-together system comprises a female portion and a male portion, one of the portions being borne by the lower face of the neck phantom 301 and the other of the portions being borne by the upper face of the base 312 so that the neck phantom 301 and the base 312 can be fitted together.

This allows the phantom 301 and the base 312 to be interlocked securely.

For preference, the fixing means further comprise adhesive arranged between the neck phantom 301 and the base 312.

The adhesive is, for example, based on polyepoxy, polymethylmethacrylate, or polycarbonate.

The base 112 is preferably made from a material that has no influence on the measurements taken from the overall phantom 300. Thus in this instance the base 112 is made of plastic. The base 112 is, for example, made of polymethylmethacrylate, of polycarbonate or alternatively of polyepoxy.

For preference, the neck phantom 301 comprises a central second housing 304 which extends along the axis A and opens on the one hand onto the upper face 303 of the neck phantom 301 and, on the other hand, onto the lower face of the neck phantom 301, and therefore of the base 312. This second housing 304 has a cross section (in a plane of section normal to the axis A) in the shape of a teardrop, the central part 305 of which is configured as an ellipse of center B arranged on the axis A and the pointed part 306 of which extends in a radial direction, in the direction away from the first housing 302.

The overall phantom 300 comprises a cervical vertebrae phantom 307, which phantom is of a shape that complements the second housing 304 and therefore extends along the axis A in the neck phantom 301. The cervical vertebrae phantom 307 is thus arranged in such a way that its lower face rests on the base 312 and that its upper face 308 is at the same level as the upper face 303 of the neck phantom 301. It will be noted that the pointed part of this cervical vertebrae phantom 307 makes it possible to simulate the spinous process.

For preference, the cervical vertebrae phantom 307 comprises a central housing 309 which extends along the axis A and opens onto the upper face 308 of the cervical vertebrae phantom 307 and onto the lower face of the cervical vertebrae phantom 307. This housing 309 has a cross section (on a plane of section normal to the axis A) that is circular with its center arranged on the axis A.

The overall phantom 300 further comprises a spinal cord phantom 310, which phantom is of a shape that complements the housing 309 and therefore extends along the axis A in the cervical vertebrae phantom 307. The spinal cord phantom 310 is thus arranged in such a way that its lower face rests on the base 312 and that its upper face 311 is at the same level as the upper face 308 of the cervical vertebrae phantom 307.

For preference, each phantom of the overall phantom 300 is made from a material suited to best simulating the physical characteristics (and in particular here the x-ray or gamma-ray transmission properties) of the organ it is supposed to represent. In the case of the neck phantom 301 and the thyroid phantom 1, a material that best simulates the human tissues is sought, as already explained. In the case of the cervical vertebrae phantom 307, a material best simulating bones is sought, and in the case of the spinal cord phantom 310, a material best simulating the spinal cord is sought.

For example, in the case of the cervical vertebrae phantom 307, a human vertebra is formed of a spongy bone surrounded by a hard (cortical) bone. If the mean density of these two bones is determined, taking into consideration the proportion of spongy bone and of cortical bone as given in the ICRP recommendations, then for an adult man a mean density of 1.427 grams per centimeter$^{-3}$ is obtained as, therefore, is a linear attenuation coefficient of 0.152 centimeter$^{-1}$ for a high energy line of 356 kiloelectron-volts (corresponding to that of the barium 133 used in this instance). The material sought therefore needs to have a linear attenuation coefficient close to that value.

In that way, the overall phantom 300 comprises the neck phantom 301, the base 312, the thyroid phantom 1, the cervical vertebrae phantom 307 and the spinal cord phantom 310.

An anthroporadiometric or nuclear medicine study can thus be conducted on the thyroid phantom 1 alone or indeed on the overall phantom 300 which has to include the thyroid phantom and all or some of the rest of the overall phantom 300.

Thus, multiple measurements can be taken under different reference conditions. Advantageously, the overall phantom 300 is more representative of a human body, making it possible to obtain better reference measurements using said phantom, notably as far as the thyroid phantom 1 is concerned.

Figure 7:
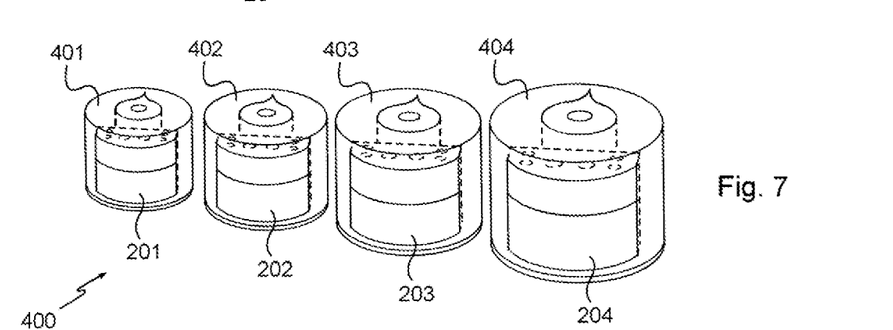
FIG. 7 is a perspective view of a series of overall phantoms each respectively comprising one of the thyroid phantoms from the family illustrated in FIG. 5.

For preference, as visible in FIG. 7, when a thyroid phantom family 200 is created as illustrated in FIG. 5, each of these thyroid phantoms is respectively inserted into an overall phantom.

This then gives an overall phantom family 400 as described hereinabove, each phantom being intended to be used as a benchmark for reference measurements for a particular patient age group category. In this instance, a family 400 of four phantoms is therefore produced, in connection with the family 200 of thyroid phantoms which is described with reference to FIG. 5: a first phantom 401 associated with a five-year-old patient, a second phantom 402 associated with a 10-year-old patient, a third phantom 403 associated with a 15-year-old patient and a fourth phantom 404 associated with an adult patient.

The dimensions of each overall phantom (and therefore of each thyroid phantom, neck phantom, cervical vertebrae phantom and spinal cord phantom as well as the base) are therefore adapted in such a way as to simulate a neck, a thyroid, a spinal cord, and cervical vertebrae of a patient of the age to which the phantom relates.

Multiple reference measurements can thus be taken. Advantageously, each overall phantom proves to be more representative of a human body of a particular category thereby making it possible to obtain better reference measurements using said phantom.

The invention is not restricted to that which has just been described, but on the contrary encompasses every alternative form that falls within the scope defined by the claims.

In particular, although here the various phantoms (thyroid phantoms and overall phantoms) are adapted to suit a particular age, the phantoms could additionally or instead also be adapted to suit a particular sex, female or male, or even additionally or instead also be adapted to suit a particular pathology notably, although not exclusively, connected with the thyroid (hyperthyroidism, etc.).

The various materials mentioned could of course differ from those described. Of course, where there is a desire to fill the cavity with a solution, care will be taken in selecting the materials for the body, for the fixing means and for the filling means, to ensure that these materials are compatible with this solution or at the very least are sufficiently resistant to this solution that the phantom will remain fluidtight and hermetically sealed and will remain so for a life of at least several years and preferably of at least one year. The solution could just as easily be liquid as semiliquid (for example could be a resin or even a gel).

Although in this instance the solution contains barium 133, the solution could instead or in addition contain any other radionuclide, particularly, although not exclusively, a radionuclide of interest in the medical fields of application (anthroporadiometry, nuclear medicine, radioprotection, etc.). The solution could thus for example contain a barium 133 and cesium 137 pair. Furthermore, the solution could comprise a radionuclide that simulates at least one of the emission lines of a radionuclide other than iodine 131, particularly, although not exclusively, a radionuclide of interest in the medical fields of application (anthroporadiometry, nuclear medicine, radioprotection, etc.) such as iodine 123.

Although here, apart from in terms of their dimensions, the thyroid phantoms within one and the same family are all identical, the phantoms could differ slightly within one and the same family. Thus, it might be preferable to have one loop passing around both lobes for the smallest sizes of phantom thyroid (for example for five-year-old children) and loops each passing around one of the lobes for thyroid phantoms of larger sizes (for example for children over five years of age and for adults). The shape of the filling canals could also be adapted to suit the volume of the cavity that is to be filled with the solution.

In the same way, although in this instance the global phantoms within one and the same family are all identical except in terms of dimensions, the phantoms within the one and the same family could differ slightly.

Although in this instance an overall phantom family is associated with a thyroid phantom family a single overall phantom could be associated with a thyroid phantom family, said overall phantom being configured in such a way as to receive individually each of the thyroid phantoms of the thyroid phantom family.

The various phantoms could differ from what has been described. For example, although here the thyroid phantom comprises a hollow cylinder, it is possible for the thyroid phantom not to comprise such a cylinder, the trachea then for example being simply represented by the space separating the lobes of the cavity. It is possible for the overall phantom not to have a base, the various phantoms then for example all being received in blind-ended housings of the neck phantoms.

The invention claimed is:

1. A thyroid phantom, the phantom comprising a body comprising at least two parts between them defining a thyroid cavity and means for fixing the two parts together to close the cavity in a sealed manner, the phantom further comprising means for filling the cavity with a solution, said filling means comprising at least one canal extending from outside the body into the cavity and means for temporarily hermetically plugging said canal.

2. The phantom as claimed in claim 1, in which the body comprises a hollow cylinder extending in the body between two lobes of the cavity without, however, passing through the cavity.

3. The phantom as claimed in claim 1, in which the body is made from a material capable of being used by a three-dimensional printer.

4. The phantom as claimed in claim 1, in which the body is configured in such a way as to exhibit the overall shape of a rectangular parallelepiped, one main lateral face being rounded.

5. The phantom as claimed in claim 1, in which the cavity is arranged in the body in such a way as to take into account a thyroid/neck distance of a human body.

6. The phantom as claimed in claim 1, in which the cavity is arranged in the body in such a way as to take into account an attenuation of rays emitted by a thyroid in tissues of a human body.

7. The phantom as claimed in claim 1, in which the fixing means comprise at least one fitting-together system comprising a female portion and a male portion, one of the portions being borne by the first part and the other of the portions being borne by the second part facing the other portion in order to allow the two portions to be fitted together.

8. The phantom as claimed in claim 7, in which the fitting-together system surrounds at least one lobe of the cavity.

9. The phantom as claimed in claim 1, in which the fixing means comprise at least one screw which secures the two body parts together in a sealed manner.

10. The phantom as claimed in claim 9, in which the fixing means further comprise adhesive arranged between the screw and an orifice in the body receiving the screw.

11. The phantom as claimed in claim 1, in which the filling means comprise a first canal extending from an upper face of the first part as far as into an upper end of a first lobe of the cavity, and a second canal extending from the upper face of the first part as far as into an upper end of a second lobe of the cavity.

12. The phantom as claimed in claim 11, in which the plugging means comprise two screws respectively plugged in one of the canals, and two seals, each seal being arranged in the relevant canal between the associated screw and said canal.

13. The phantom as claimed in claim 1, in which the phantom comprises a solution filling the cavity of the thyroid phantom.

14. The phantom as claimed in claim 13, in which the solution is a radioactive solution.

15. The phantom as claimed in claim 14, in which the solution comprises at least one radionuclide simulating at least one of the emission lines of iodine 131 and having a longer lifetime than iodine 131.

16. A method for producing a phantom as claimed in claim 1, comprising the following successive steps:
- three-dimensional digital modeling of the body of the thyroid phantom,
- separate manufacture of each part of the body by three-dimensional printing using a 3D printer,
- cleaning, off each part of the body thus created, a lost material used by the 3D printer to form the cavity,
- forming various orifices and housings intended to receive the plugging means and the fixing means,
- assembling the two parts of the body with one another.

17. A thyroid phantom family comprising at least two thyroid phantoms as claimed in claim 1, each thyroid phantom being suited to simulating at least the thyroid of a distinct particular category of human beings.

18. An overall phantom comprising a thyroid phantom as claimed in claim 1, the overall phantom comprising a neck phantom receiving the thyroid phantom, a cervical vertebrae phantom received in the neck phantom and a spinal cord phantom received in the cervical vertebrae phantom.

19. The overall phantom as claimed in claim 18, further comprising a base on which the neck phantom is arranged.

20. An overall phantom family comprising at least two overall phantoms as claimed in claim 18, each overall phantom being suited to simulating at least the thyroid of a distinct particular category of human beings.

* * * * *